(12) United States Patent
Dong

(10) Patent No.: US 6,383,201 B1
(45) Date of Patent: May 7, 2002

(54) SURGICAL PROSTHESIS FOR REPAIRING A HERNIA

(76) Inventor: Tennison S. Dong, 17220 Newhope St. (Suite 120), Huntington Beach, CA (US) 92708

( * ) Notice: Subject to any disclaimer, the term of this patent is extended or adjusted under 35 U.S.C. 154(b) by 0 days.

(21) Appl. No.: 09/312,526

(22) Filed: May 14, 1999

(51) Int. Cl.[7] .............................................. A61B 17/08
(52) U.S. Cl. ..................... 606/151; 606/215; 623/23.76
(58) Field of Search ................................ 606/213, 215, 606/115, 151; 623/23.58, 23.72, 23.76

(56) References Cited

U.S. PATENT DOCUMENTS

| 2,671,444 A | 3/1954 | Pease, Jr. |
| 4,187,390 A | 2/1980 | Gore |
| 4,769,038 A | 9/1988 | Bendavid et al. |
| 5,254,133 A | 10/1993 | Seid |
| 5,263,970 A | 11/1993 | Preller |
| 5,445,597 A | 8/1995 | Clark et al. |
| 5,593,441 A | 1/1997 | Lichenstein et al. |
| 5,634,931 A | 6/1997 | Kugel |
| 5,634,944 A | * 6/1997 | Magram |
| 5,697,978 A | 12/1997 | Sgro |
| 5,725,577 A | 3/1998 | Saxon |
| 5,743,917 A | 4/1998 | Saxon |
| 5,769,864 A | 6/1998 | Kugel |

FOREIGN PATENT DOCUMENTS

WO   WO 97/35533 A1   10/1997

* cited by examiner

Primary Examiner—Corrine McDermott
Assistant Examiner—Brian E. Pellegrino
(74) Attorney, Agent, or Firm—Richard E. Bee

(57) ABSTRACT

A surgical prosthesis for repairing a hernia in a sturdy tension-free manner. The prosthesis includes a layer of adhesion resistant material and a first layer of tissue ingrowth receptive mesh material affixed to the layer of adhesion resistant material. A second layer of tissue ingrowth receptive mesh material is positioned adjacent the first layer of tissue ingrowth receptive mesh material and a connecting thread is interwoven between the midsections of the layers for forming a midsectional seam fastening together the three layers. The prosthesis is implanted in the hernial area of the patient in such a manner as to duplicate the structure of the original unherniated fascial tissue. The adhesion resistant layer faces inwardly to prevent adhesion of internal body viscera to the prosthesis.

15 Claims, 5 Drawing Sheets

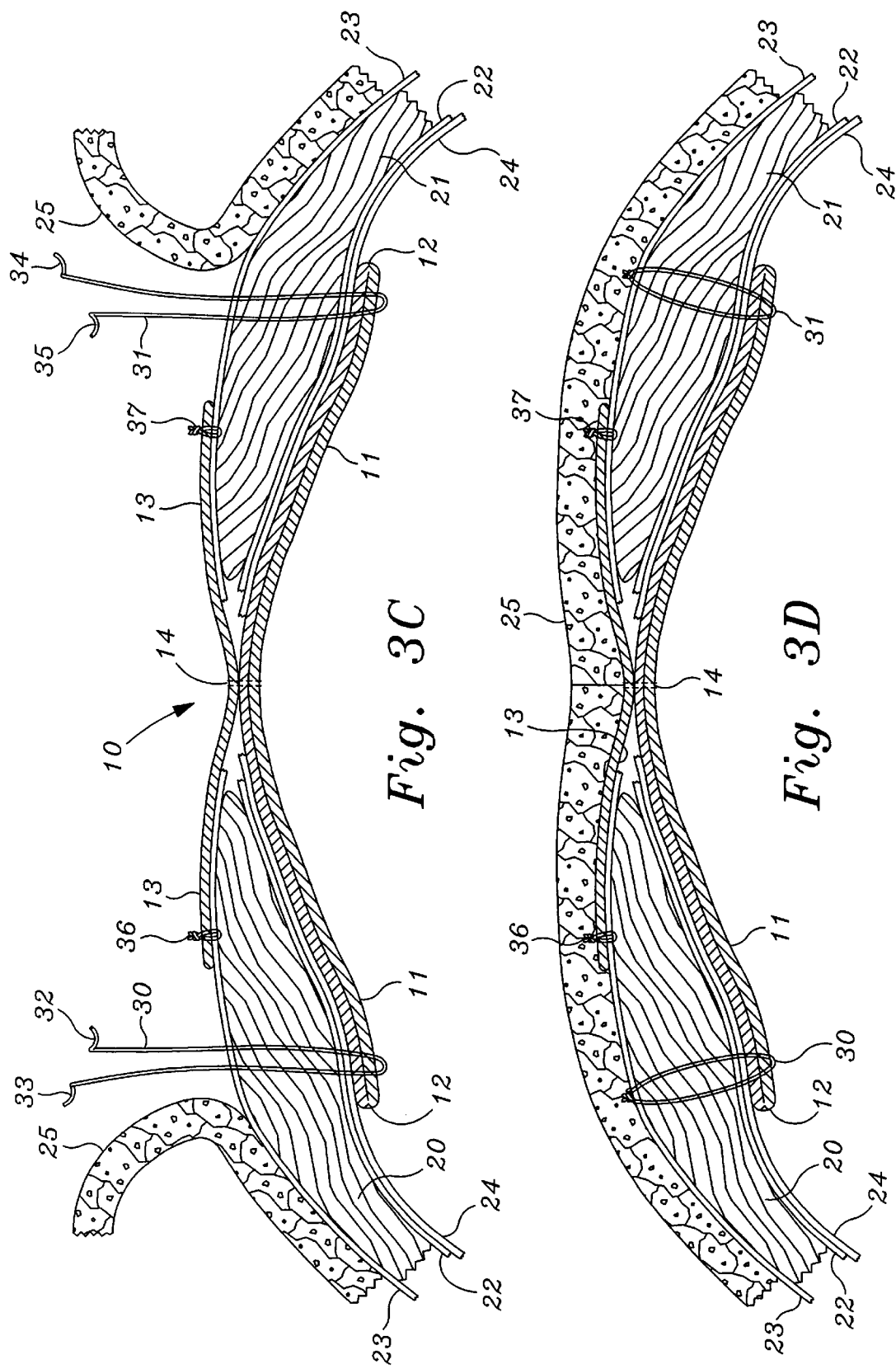

SURGICAL PROSTHESIS FOR REPAIRING A HERNIA

DESCRIPTION

TECHNICAL FIELD

This invention relates to surgical prostheses for repairing abdominal hernias and is particularly useful for repairing ventral, large umbilical and recurrent hernias.

BACKGROUND OF THE INVENTION

A hernia is a rupture of the abdominal wall which provides support for internal body organs. A rupture or undesired weakening in the abdominal wall is not normally, of itself, a problem. The problem is the ensuing bulge of intestine and/or omentum which pushes its way through the opening. A conventional procedure for repairing a hernia involves making an incision over the site of the hernia, pushing the internal viscera back into the abdominal cavity and closing the opening by stitching or suturing one side firmly to the other. Unfortunately, this suturing distorts sensitive tissue, causes tension and subsequent pain, and renders the repair site susceptible to a recurrent hernia.

An alternative procedure which appears to be gaining popularity involves making the incision, placing a piece of knitted mesh material over the hernial opening, holding or suturing the mesh material firmly in place and closing the incision. If properly done, there is less tissue distortion and less tension on the tissue adjacent the opening. Thus, the results are better and the patient is frequently able to resume his normal activities sooner. While this mesh approach appears to be a step in the right direction, there is, nevertheless, room for further improvement, particularly in regards to providing a tension-free repair of greater strength.

SUMMARY OF THE INVENTION

The present invention provides an improved surgical prosthesis for repairing a ventral hernia. This improved prosthesis is a two piece mesh device designed to include a dual or combined layer of adhesion resistant material fused inferiorly to a superior piece of tissue ingrowth receptive mesh material, this dual layer being fastened centrally to a single and separate layer of tissue ingrowth receptive mesh material. The centrally fastening midsectional seam provides stability to the prosthesis and allows the mesh material to envelope the muscular abdominal wall, both externally and internally, with minimal tension.

When the prosthesis is implanted into the patient, the superior surface of the fused dual layer is positioned against the peritoneal surface of the abdominal cavity. This allows the tissue ingrowth receptive mesh to become firmly incorporated with the body tissue. The adhesion resistant surface of the dual layer faces the internal organs and infinitely decreases the incidence of adhesions and/or bowel obstruction. The single layer of this two piece device is positioned between the anterior fascia of the abdominal wall musculature and the subcutaneous tissue. The ingrowth receptive nature of this single layer enables incorporation of this layer with both adjoining abdominal structures.

For a better understanding of the present invention, together with other and further advantages and features thereof, reference is made to the following description taken in connection with the accompanying drawings, the scope of the invention being pointed out in the appended claims.

BRIEF DESCRIPTION OF THE DRAWINGS

Referring to the drawings:

FIG. 3C is a cross-sectional view showing the skin and fat layer peeled back and the prosthesis implanted and deployed in the hernial opening of FIG. 3B;

FIG. 3D is a cross-sectional view corresponding to FIG. 3C after the skin and fat layer has been returned to its normal closed position;

DETAILED DESCRIPTION OF THE ILLUSTRATED EMBODIMENT

Figure 1:
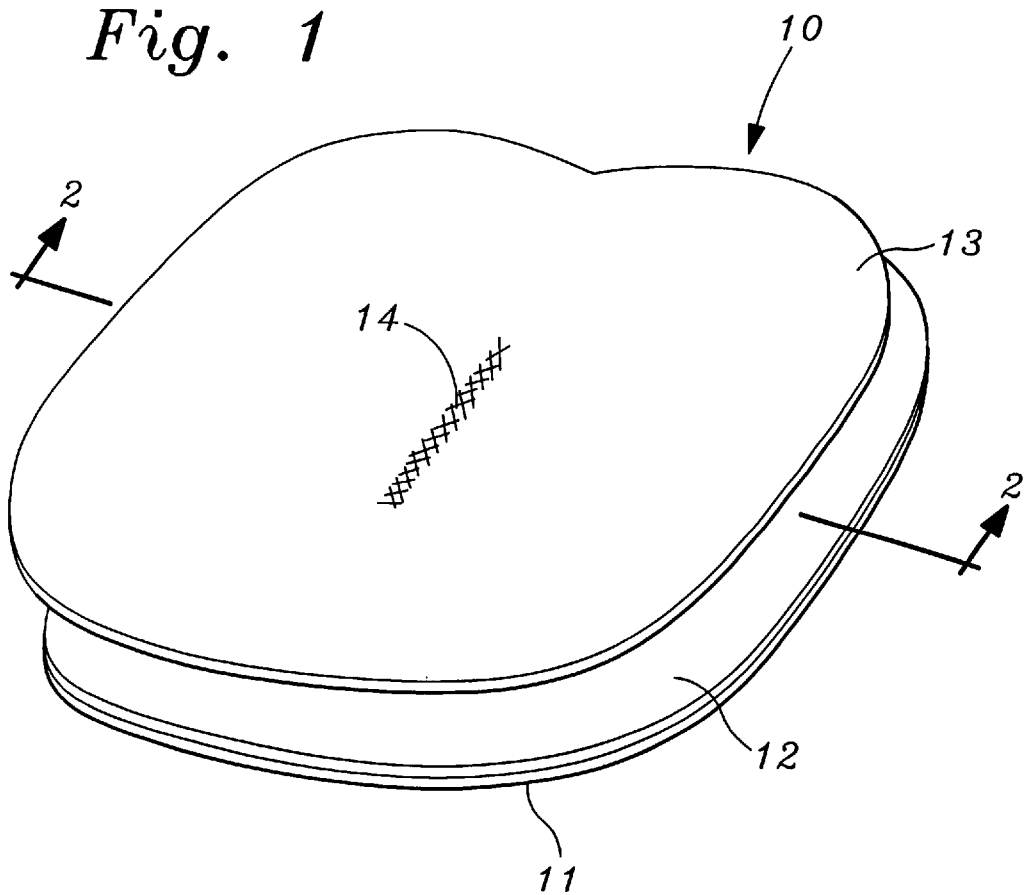
FIG. 1 is a perspective view of a representative embodiment of a surgical prosthesis constructed in accordance with the present invention.
Figure 2:
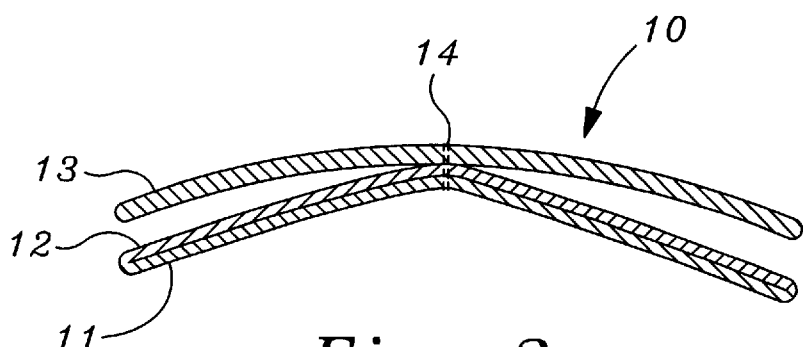
FIG. 2 is a cross-sectional view of the FIG. 1 prosthesis, taken along section line 2—2 of FIG. 1.

Referring to FIGS. 1 and 2, there is shown a surgical prosthesis 10 which is particularly useful for repairing a hernia in the ventral region of a human body. Prosthesis 10 includes a layer of adhesion resistant material 11 and a first layer of tissue ingrowth receptive mesh material 12 positioned adjacent the layer of adhesion resistant material 11. Preferably, the layer 12 is affixed to the layer 11 so as to form a more or less unitary combined layer or dual layer. This affixing may be accomplished by placing an adhesive material between the layers or by thermally bonding the two layers together or by a stitching or sewing together of the two layers. In so doing, care must be taken so as not to cause any major impairment of the mesh-like quality of the mesh material forming the layer 12. Layers 11 and 12 are coextensive in area and are larger in area than the hernial opening it is desired to repair.

Prosthesis 10 also includes a second and separate layer of tissue ingrowth receptive mesh material 13 positioned adjacent the first layer of tissue ingrowth receptive material 12. This second mesh layer 13 may be, but need not be, coextensive in area with the combined layers 11 and 12. Layer 13, however, should be larger in area than the hernial opening to be repaired. When manufacturing the prosthesis 10, the second mesh layer 13 is preferably made the same size as layers 11 and 12, leaving the surgeon the option of trimming it down to a smaller size if desired.

Prosthesis 10 further includes a fastening mechanism for fastening together the midsections of layers 11, 12 and 13. In the illustrated embodiment, this fastening mechanism takes the form of a connecting thread 14 interwoven between the midsections of layers 11, 12 and 13 for forming a midsectional seam fastening together the three layers.

Figure 3A:
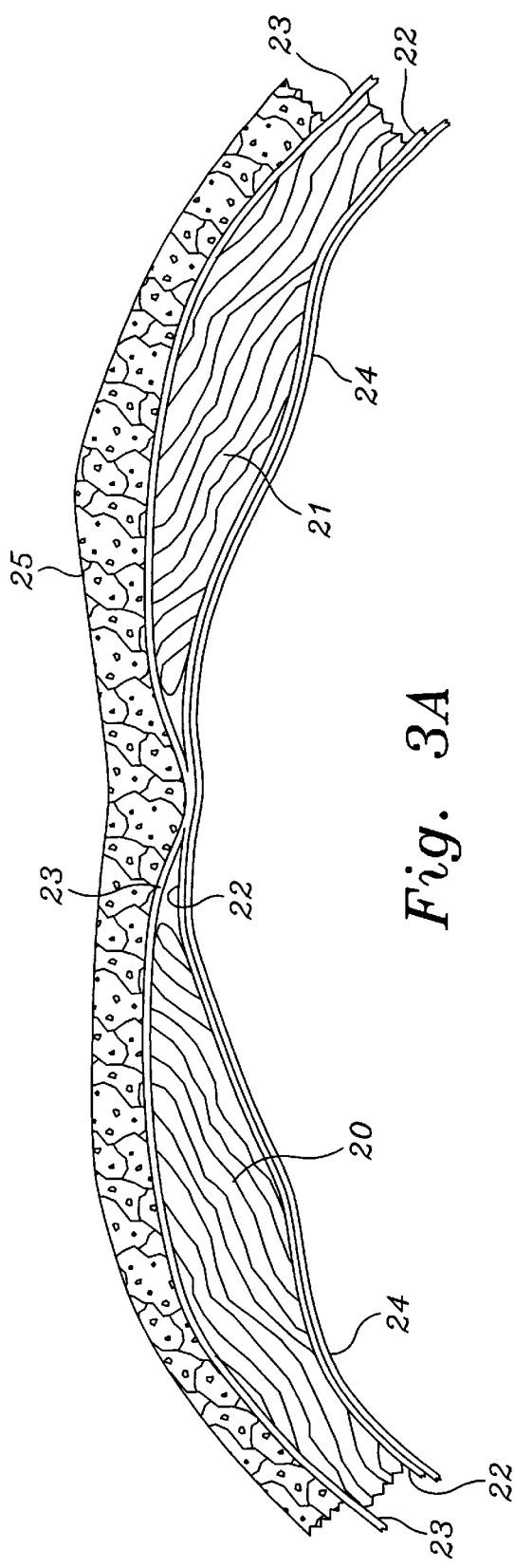
FIG. 3A is a cross-sectional view of a normal, unherniated anterior abdominal wall of a human body taken in the ventral region of the body.

Referring to FIG. 3A, there is shown a cross-sectional view of a normal, unherniated anterior abdominal wall of a human body taken in the ventral region of the body. As there shown, the abdominal wall includes left and right rectus muscles 20 and 21 enclosed and held in place by interior and exterior layers of fascia 22 and 23. These layers of fascia, a thin but strong fibrous tissue, merge together in the region intermediate the rectus muscles 20 and 21. A layer 24, called the peritoneum, covers the interior side of the interior fascia 22. The peritoneum 24 is a softer, more pliable layer of tissue material and provides a sack-like enclosure for the intestines and other internal viscera. A layer of skin and subcutaneous fat 25 covers the exterior of the exterior fascia 23 and forms the exterior of the body structure.

Figure 3B:
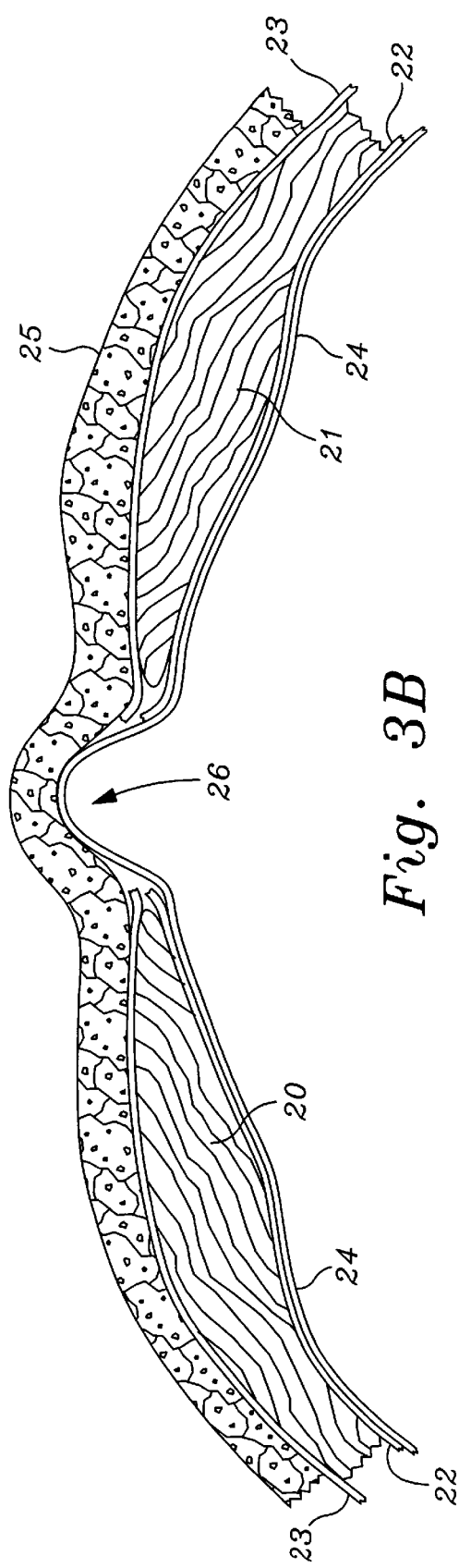
FIG. 3B is a cross-sectional view corresponding to FIG. 3A but showing the presence of a hernia.

FIG. 3B shows the occurrence of a hernia, the hernial opening being indicated at 26. In this example, the hernia is represented by the rupture or breakage of the fascia layers 22 and 23 in the region intermediate the rectus muscles 20 and 21. This breakage allows the internal viscera to push the peritoneum 24 in an outward direction, creating a noticeable bulge in the skin 25. If not treated, the condition will only worsen with time, with the peritoneal bulge becoming larger. Eventually, most of the intestine may become incarcerated in the hernia sac.

FIG. 3C shows how the prosthesis 10 is implanted into the patient's body to repair the hernia. An incision is made through the skin and subcutaneous fat 25, the skin and fat 25 are peeled back, the internal viscera is returned to where it belongs, an incision is made in the peritoneum 24 and the prosthesis 10 is inserted into the hernial opening and deployed as shown. In particular, the combined or dual layer 11, 12 is spread out internally of and adjacent to the peritoneum 24 with the adhesion resistant layer 11 facing the internal viscera. The second and separate layer of tissue ingrowth receptive mesh material 13 is spread out externally of and adjacent to the external fascia 23. The prosthesis 10 is positioned so that the hernial opening is covered and the midsectional seam 14 is centrally located in and extends along the space between the left and right rectus muscles 20 and 21.

FIG. 3D shows the hernial area after completion of the surgery. Sutures 30, 31, 36 and 37 are placed as shown, at a first longitudinal body location. Sutures 30 and 31 secure the inner dual layer 11, 12 of the prosthesis 10 to the abdominal wall structure, as shown. These sutures 30 and 31 may be installed from below by using a double needle technique. Sutures 36 and 37, on the other hand, secure the second mesh layer 13 to the outer fascial layer 23. All of sutures 30, 31, 36 and 37 are located so that no lateral tension is placed on either of the fascia layers 22 and 23 or on the rectus muscles 20 and 21. Additional sets of sutures are placed at other longitudinal body locations. In particular, it is desired that the four corners areas of prosthesis 10 be securely fastened to the abdominal wall structure.

After completion of the suturing, the skin and fat layer 25 is returned to its normal position, as shown in FIG. 3D. The incisional edges of the skin and fat layer 25 may be secured to one another by appropriate subsurface sutures (not shown).

A point to note is that the separate mesh layer 13 in FIGS. 3C and 3D is of lesser size than the dual layer 11, 12. This is a result of trimming of layer 13 by the surgeon prior to installation of the prosthesis 10.

Figure 4:
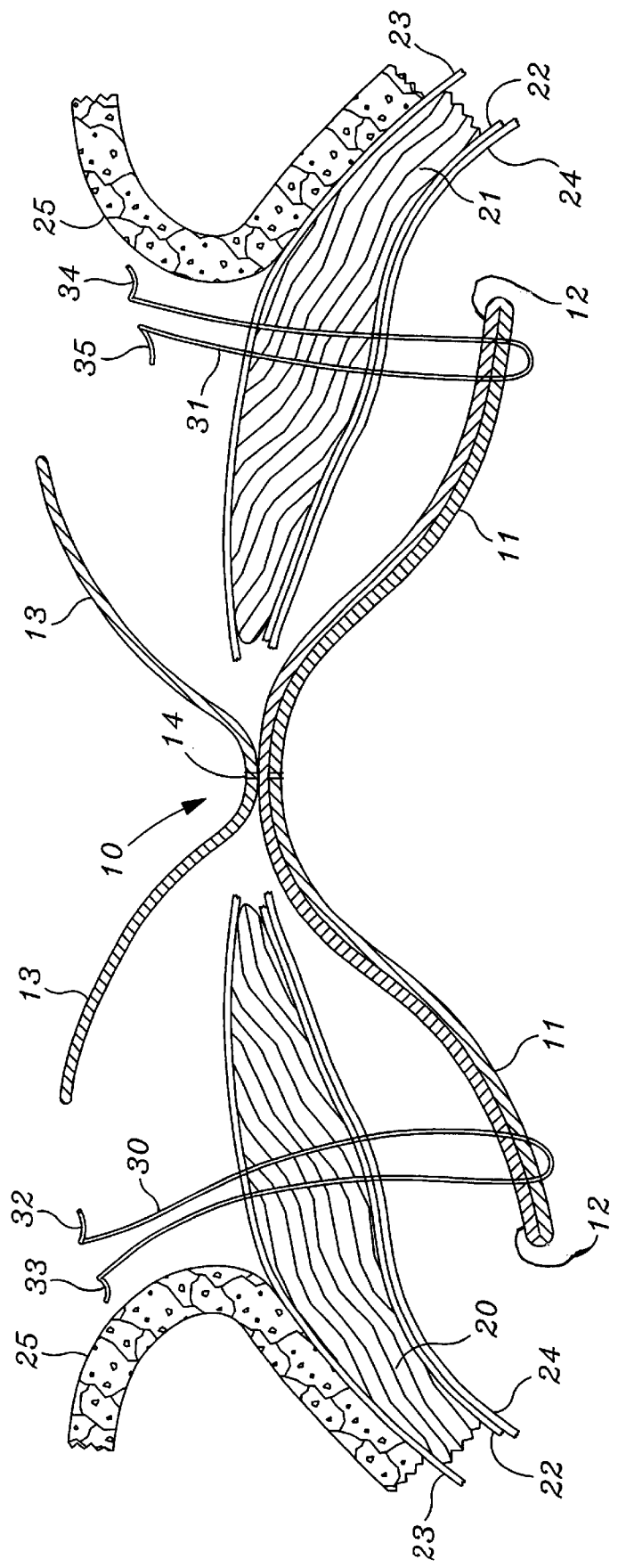
FIG. 4 is a cross-sectional view corresponding to FIG. 3C before the prosthesis is completely implanted and is used to explain how sutures are placed from within the abdominal cavity using a double needle technique.

FIG. 4 is a cross-sectional view corresponding to FIG. 3C before the prosthesis 10 is completely implanted and is used to explain how the longer sutures, like sutures 30 and 31, are installed from within the abdominal cavity using a double needle technique. Suturing needles 32 and 33 are fastened to the two ends of suture 30 and suturing needles 34 and 35 are fastened to the two ends of suture 31.

Figure 5:
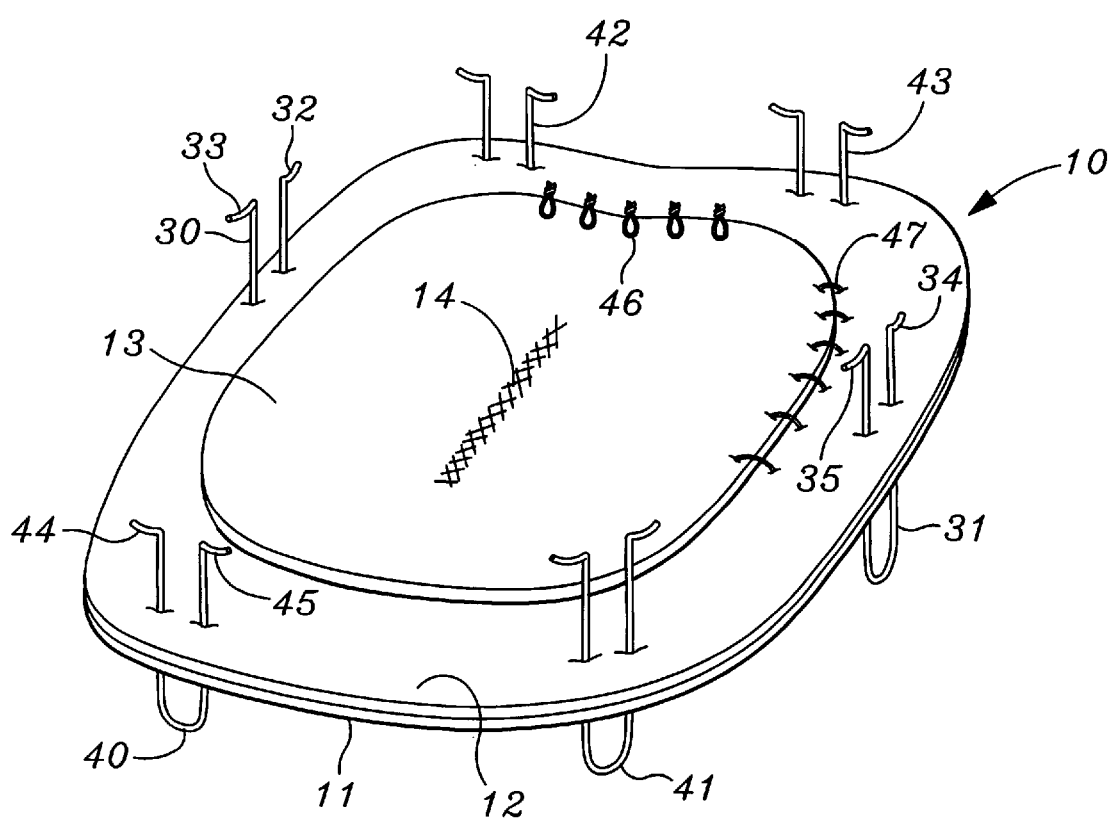
FIG. 5 is a perspective view showing a representative manner in which multiple sutures may be located at various positions on the prosthesis.

FIG. 5 is a perspective view of the prosthesis 10 of FIGS. 3C and 3D and shows a representative manner in which multiple sutures may be located at various positions on the prosthesis 10. In particular, sutures 30 and 31 are located on the left and right sides and additional long sutures 40–3 are positioned in the four corner areas of the dual layer 11, 12. All long sutures have suturing needles attached to the two ends thereof, for example, needles 44 and 45 for suture 40. The long sutures 30, 31 and 40–43 are preferably inserted through the dual layer 11, 12 in the manner shown in FIG. 5 before the prosthesis 10 is placed in the incisional area. The prosthesis 10 is thereafter positioned in the hernial opening with the dual layer 11, 12 and the single layer 13 in a loose, more or less open condition, as indicated in FIG. 4. The surgeon inserts his fingers into the hernial opening and, one suture at a time, grasps the pair of needles for each long suture and forces them upwardly through the peritoneum 24, the inner fascia 22, the rectus muscle and the outer fascia 23. After insertion through the abdominal structure, the long sutures are left loose and dangling, in the manner shown in FIG. 4 for sutures 30 and 31, until after all long sutures have been installed. After all long sutures have been installed, they are drawn up tight and tied off in the manner shown for sutures 30 and 31 in FIG. 3D, the excess suture length being cut off and removed, along with the attached needles.

After attachment of the dual layer 11, 12, the single or outer layer 13 of prosthesis 10 is attached to the outer fascia layer 23. One manner of doing this is by means of short sutures, such as represented by sutures 36 and 37 in FIG. 3D and sutures 46 in FIG. 5. Another manner of doing this is by means of fascial staples, as represented by staples 47 in FIG. 5. These short sutures and/or staples are installed from the exterior side of the abdominal structure in a conventional manner. After completion of the suturing, the skin and fat layer 25 is returned to its normal position, as shown in FIG. 3D.

What happens after installation of the prosthesis 10 is of particular interest. The body tissue, particularly the fascia 22 and 23 and the peritoneum 24 commence to incorporate themselves into the mesh structure of the mesh layers 12 and 13 of the prosthesis 10. Sensing the presence of the mesh material, the body tissue sends out fibrous tissue which grows in, around and through and thoroughly entwines itself with the prosthesis mesh material 12 and 13. In this manner, the prosthesis 10 becomes securely attached to and, in effect, becomes an integral part of the host body tissue. This provides a very strong repair with little likelihood of a recurrent hernia.

A primary purpose of the sutures, such as sutures 30, 31, 36, 37, 40–43 and 46, are to prevent rotation or migration of the prosthesis 10 during the tissue ingrowth process. In addition, the geometry of the prosthesis 10 is such that it tends to keep itself properly positioned for the duration of the tissue incorporation process. The pressure exerted by the abdominal viscera keeps the dual layer 11, 12 of the prosthesis 10 in place against the underside of the peritoneum 24, the skin and fat layer 25 keeps the separate mesh layer 13 in place against the outer fascia layer 23 and the midsectional seam 14 resists rotation or migration of the prosthesis 10. After the tissue ingrowth process, the prosthesis 10 is securely attached to the fascia and the hernial area is, in most cases, stronger than a corresponding healthy, unherniated abdominal structure.

A point to note is that the geometry of the prosthesis 10, when implanted in the human body (as illustrated in FIG. 3D), closely resembles the geometry of the original unherniated fascial structure. And substantially no lateral tension is placed on the fascia or the rectus muscles. Thus, the hernial area is restored to its original pristine condition.

The layer of adhesion resistant material 11 serves to prevent any adhesion of the internal body viscera to the prosthesis 10. A suitable material for fabrication of the adhesion resistant layer 11 is any one of the following materials: a polytetrafluoroethylene polymer material of the type distributed by W. L. Gore & Associates, Inc. of Newark, Del. under the trade name "Gore-Tex"; a silicone elastomer material of the type distributed by Dow Corning Corporation of Midland, Mich. under the trade name "Silastic"; and a Teflon material of the type distributed by E. I. Du Pont de Nemours and Company of Wilmington, Del.

A suitable material for fabrication of the first and second layers of tissue ingrowth receptive mesh material 12 and 13 is any one of the following materials: a polypropylene mesh material of the type distributed by C. R. Brad, Inc. of Murray Hill, N.J. under the trade name "Marlex"; a polyethylene mesh material of the type distributed by E. I. Du Pont de Nemours and Company of Wilmington, Del. under the trade name "Alathon"; and a Dacron mesh material or a Nylon mesh material of the type distributed by E. I. Du Pont de Nemours and Company of Wilmington, Del.

If the seam forming connecting thread 14 of the prosthesis 10 is to be exposed to the internal viscera, then it should be made of adhesion resistant material. In such case, it may be, for example, a thread of polytetrafluoroethylene polymer material of the type sold under the trade name "Gore-Tex" by W. L. Gore & Associates, Inc.

While there have been described what are at present considered to be preferred embodiments of this invention, it will be obvious to those skilled in the art that various changes and modifications may be made therein without departing from the invention and it is, therefore, intended to cover all such changes and modifications as come within the true spirit and scope of the invention.

What is claimed is:

1. A surgical prothesis for repairing a hernia comprising:
   a layer of adhesion resistant material;
   a first layer of tissue ingrowth receptive mesh material affixed to the layer of adhesion resistant material;
   a second layer of tissue ingrowth receptive mesh material positioned adjacent the first layer of tissue ingrowth receptive mesh material;
   and connecting thread interwoven between the midsections of at least the two layers of mesh material for forming a midsectional seam fastening together the two layers of mesh material.

2. A surgical prothesis in accordance with claim 1 wherein the layer of adhesion resistant material is a layer of material selected from the group of materials consisting of polytetrafluoroethylene material, silicone elastomer material and Teflon material.

3. A surgical prosthesis in accordance with claim 1 wherein the layer of adhesion resistant material is a layer of polytetrafluoroethylene polymer material.

4. A surgical prosthesis in accordance with claim 1 wherein the first and second layers of tissue ingrowth receptive mesh material are layers of mesh material selected from the group of materials consisting of polypropylene mesh material, polyethylene mesh material, Dacron mesh material and nylon mesh material.

5. A surgical prosthesis in accordance with claim 1 wherein the first and second layers of tissue ingrowth receptive mesh material are layers of polypropylene mesh material.

6. A surgical prosthesis in accordance with claim 1 wherein the first layer of tissue ingrowth receptive mesh material is affixed to the layer of adhesion resistant material by an adhesive material.

7. A surgical prosthesis in accordance with claim 1 wherein the first layer of tissue ingrowth receptive mesh material is affixed to the layer of adhesion resistant material by thermal bonding of the two layers.

8. A surgical prosthesis in accordance with claim 1 wherein the first layer of tissue ingrowth receptive mesh material is affixed to the layer of adhesion resistant material by a stitching together of the two layers.

9. A surgical prosthesis in accordance with claim 1 wherein the connecting thread is interwoven between the midsections of the layer of adhesion resistant material and the two layers of mesh material for forming a midsectional seam fastening together all three layers.

10. A surgical prosthesis in accordance with claim 9 wherein the connecting thread is a thread of adhesion resistant material.

11. A surgical prosthesis in accordance with claim 9 wherein the connecting thread is a thread of polytetrafluoroethylene polymer material.

12. A surgical prosthesis for repairing a ventral hernia wherein the fascia enclosing the rectus muscles is ruptured, such prosthesis comprising:
    a dual layer having a layer of adhesion resistant material and a layer of tissue ingrowth receptive mesh material affixed to one another, both layers being coextensive and larger in area than the hernial opening;
    a single and separate layer of tissue ingrowth receptive mesh material positioned adjacent the dual layer on the mesh material side thereof, this separate layer being larger in area than the hernial opening;
    and connecting thread interwoven between the midsections of at least the two layers of mesh material for forming a midsectional seam fastening together the two layers of mesh material;
    the prosthesis being adapted to be inserted into the hernial opening with the dual layer being spread out internally of and adjacent to the peritoneum with the adhesion resistant side facing the internal abdominal viscera and with the separate layer of tissue ingrowth receptive mesh material being spread out externally of and adjacent to the external fascia with the midsectional seam located in and extending along the space between the right and left rectus muscles, whereby the prosthesis structure corresponds to the original unherniated fascial structure.

13. A surgical prosthesis in accordance with claim 12 wherein the connecting thread is interwoven between the midsections of the layer of adhesion resistant material and the two layers of mesh material for forming a midsectional seam fastening together all three layers.

14. A surgical prosthesis in accordance with claim 13 wherein the connecting thread is a thread of adhesion resistant material.

15. A surgical prosthesis in accordance with claim 12 wherein the layer of adhesion resistant material is a layer of polytetrafluoroethylene polymer material and the two layers of tissue ingrowth receptive mesh material are layers of polypropylene mesh material.

* * * * *